(12) United States Patent
Akah et al.

(10) Patent No.: US 11,959,031 B2
(45) Date of Patent: Apr. 16, 2024

(54) CONVERSION OF WHOLE CRUDE TO VALUE ADDED PETROCHEMICALS IN AN INTEGRATED REACTOR PROCESS

(71) Applicant: Saudi Arabian Oil Company, Dhahran (SA)

(72) Inventors: Aaron Chi Akah, Dhahran (SA); Essa Alnaimi, Dhahran (SA); Qi Xu, Dhahran (SA); Musaed Salem Al-Ghrami, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 12 days.

(21) Appl. No.: 17/947,744

(22) Filed: Sep. 19, 2022

(65) Prior Publication Data

US 2024/0093103 A1 Mar. 21, 2024

(51) Int. Cl.
*C10G 67/04* (2006.01)
*C07C 2/76* (2006.01)
(Continued)

(52) U.S. Cl.
CPC .............. *C10G 67/049* (2013.01); *C07C 2/76* (2013.01); *C07C 4/04* (2013.01); *C07C 5/321* (2013.01); *C10G 9/005* (2013.01); *C10G 2300/1033* (2013.01); *C10G 2300/206* (2013.01); *C10G 2300/4006* (2013.01);
(Continued)

(58) Field of Classification Search
None
See application file for complete search history.

(56) References Cited

U.S. PATENT DOCUMENTS 3,193,486 A * 7/1965 Payne .................... C10G 51/02
 208/50
3,475,327 A * 10/1969 Eng ........................ C10G 45/02
 208/211

(Continued)

OTHER PUBLICATIONS

Notification of Transmittal of the International Search Report and Written Opinion of the International Searching Authority, or the Declaration dated Dec. 18, 2023 pertaining to International application No. PCT/US2023/074424 filed Sep. 18, 2023, pp. 1-13.

*Primary Examiner* — In Suk C Bullock
*Assistant Examiner* — Alyssa L Cepluch
(74) *Attorney, Agent, or Firm* — DINSMORE & SHOHL LLP

(57) ABSTRACT

An integrated process and associated system for conversion of crude oil to value added petrochemicals. The process includes separating crude oil into light and heavy crude fractions and processing the heavy fraction in a solvent deasphalting unit and a delayed coker unit, and then providing the light fraction and selected effluents of the solvent deasphalting unit and the delayed coker unit to a hydrotreater. The process further includes separating the effluent of the hydrotreater to generate a C1 fraction passed to a methane cracker, a C2 fraction passed to an ethane steam cracker, a C3-C4 fraction passed to a dehydrogenation reactor, a hydrotreated light fraction passed to an aromatization unit, and a hydrotreated heavy fraction passed to a steam enhanced catalytic cracking unit. The process further includes separating effluents of the various unit operations into product streams including a BTX stream and a light olefin stream.

17 Claims, 3 Drawing Sheets

(51) Int. Cl.
  *C07C 4/04*   (2006.01)
  *C07C 5/32*   (2006.01)
  *C10G 9/00*   (2006.01)

(52) U.S. Cl.
  CPC . *C10G 2300/4012* (2013.01); *C10G 2400/20* (2013.01); *C10G 2400/30* (2013.01)

(56) References Cited

U.S. PATENT DOCUMENTS

| | | | |
|---|---|---|---|
| 7,491,315 B2 | 2/2009 | Eng et al. | |
| 8,631,311 B1 | 1/2014 | Chan et al. | |
| 8,685,232 B2 | 4/2014 | Mandal et al. | |
| 8,932,451 B2* | 1/2015 | Strauss | B01J 23/74 208/92 |
| 9,228,140 B2 | 1/2016 | Abba et al. | |
| 10,316,258 B2 | 6/2019 | Rispoli et al. | |
| 10,407,630 B2 | 9/2019 | Al-Ghamdi et al. | |
| 10,472,580 B2 | 11/2019 | Al-Ghamdi et al. | |
| 10,590,354 B2 | 3/2020 | Pradeep et al. | |
| 10,717,941 B2 | 7/2020 | Al-Ghamdi et al. | |
| 2013/0224106 A1* | 8/2013 | Basset | C07C 2/76 585/700 |
| 2013/0228496 A1* | 9/2013 | Bourane | C10G 21/003 208/86 |
| 2016/0130505 A1 | 5/2016 | Baker | |
| 2016/0368838 A1 | 12/2016 | Ward et al. | |
| 2017/0058214 A1 | 3/2017 | Oprins et al. | |
| 2017/0121613 A1* | 5/2017 | Oprins | C10G 65/12 |
| 2018/0187106 A1 | 7/2018 | Abudawoud | C10G 67/00 |
| 2018/0291287 A1* | 10/2018 | Brown | C10G 21/003 |
| 2018/0305623 A1* | 10/2018 | Al-Ghrami | C10G 51/06 |
| 2020/0115645 A1 | 4/2020 | Al-Ghamdi et al. | |
| 2021/0246388 A1 | 8/2021 | Koseoglu | |
| 2022/0064556 A1 | 3/2022 | Akah et al. | |

\* cited by examiner

CONVERSION OF WHOLE CRUDE TO VALUE ADDED PETROCHEMICALS IN AN INTEGRATED REACTOR PROCESS

TECHNICAL FIELD

The present disclosure relates to an integrated process and associated system for conversion of crude oil to value added petrochemicals.

BACKGROUND

Aromatics such as BTX (benzene, toluene, and xylenes) and olefins are valuable chemicals frequently utilized in the production of many materials and formulation of many consumer goods. For example, BTX compounds are frequently utilized during the processing or production of petroleum products and during the production of consumer goods such as paints and lacquers, thinners, fuels, rubber products, adhesives, inks, cosmetics and pharmaceutical products. Similarly, light olefins are the building blocks for many modern plastic products. As such, plentiful, efficient, and economical production of both light olefins and BTX is generally desirable.

It is desirable to be able to efficiently convert whole crude oil into light olefins and BTX in view of the current and expected increasing demand for such valuable chemicals. However, existing refining systems and processes do not maximize the market value from crude oil streams and result in an undesirable volume of lower value products during production of light olefins and BTX.

SUMMARY

Accordingly, there is a clear and long-standing need to provide an efficient and economical process for the production of light olefins and BTX from a feedstock comprising substantial quantities of whole crude oil. The process and system of the present disclosure address this clear and long-standing need by utilizing processes and systems specifically to produce light olefins and BTX from crude oil by optimizing the feedstock provided to each unit operation within the integrated system. Specifically, hydrocarbon stream are separated or split with each fraction send to a reactor or other unit operation which can most effectively convert the feed provided to the reactor into BTX or light olefins or precursors chemicals to form BTX or light olefins.

In accordance with one or more embodiments of the present disclosure, an integrated process for conversion of crude oil to value added petrochemicals is disclosed. The process includes (i) providing a hydrocarbon stream comprising the crude oil to a feed separator to separate the hydrocarbon stream into a light crude fraction boiling at a first temperature or less and a heavy crude fraction boiling at greater than the first temperature, wherein the first temperature is between 190 and 210° C., (ii) providing the heavy crude fraction boiling at a temperature greater than the first temperature from the feed separator to a solvent deasphalting unit, wherein residue heavy components having a boiling points above 300° C. and asphaltenes are removed from the heavy crude fraction to generate a pitch product comprising the asphaltenes and residue heavy components and a deasphalted oil product; (iii) providing the pitch product to a delayed coker unit, wherein the pitch product undergoes a thermal cracking reaction to obtain solid petroleum coke and a delayed coker product stream comprising C1-C4 light gases, coker naphtha, and coker gas oil, (iv) providing the light crude fraction boiling at the first temperature or less, the deasphalted oil product, and the delayed coker product stream to a hydrotreater, wherein the light crude fraction, the deasphalted oil product, and the delayed coker product stream are hydrotreated to remove heteroatoms and saturate carbon-carbon bonds to generate a hydrotreater product stream; (v) providing the hydrotreater product stream to a first separator unit, wherein the hydrotreater product stream is separated into a C1 fraction, a C2 fraction, a C3-C4 fraction, a hydrotreated light fraction comprising C5 hydrocarbons to hydrocarbons boiling at than a second temperature, and a hydrotreated heavy fraction comprising hydrocarbons boiling at or greater than the second temperature, wherein the second temperature is between 200 and 215° C.; (vi) providing the C1 fraction to a methane cracker, wherein the C1 fraction is converted to a hydrogen stream and a fixed carbon stream; (vii) providing the C2 fraction to an ethane steam cracker, wherein the C2 fraction is cracked to generate an ethane steam cracker product stream comprising light olefins and aromatics; (viii) providing the C3-C4 fraction to a dehydrogenation reactor, wherein the C3-C4 fraction is dehydrogenated to generate a dehydrogenated product stream comprising propylene and butenes generated from propane and butanes in the C3-C4 fraction; (ix) providing the hydrotreated light fraction comprising C5 hydrocarbons to hydrocarbons boiling at less than the second temperature to an aromatization unit, wherein the aromatization unit converts aliphatic hydrocarbons in the hydrotreated light fraction to aromatics to generate an aromatization product stream, (x) providing the hydrotreated heavy fraction comprising hydrocarbons boiling at the second temperature or greater to a steam enhanced catalytic cracking unit, wherein the hydrotreated heavy fraction is cracked to generate a SECC product stream comprising light olefins, and (xi) providing the ethane steam cracker product stream, the dehydrogenated product stream, the aromatization product stream, and the SECC product stream to a second separator unit, wherein the second separator unit splits the ethane steam cracker product stream, the dehydrogenated product stream, the aromatization product stream, and the SECC product stream into a hydrogen fraction, a C1 stream, a C2 stream, a C3-C4 alkane stream, a light olefin stream, a BTX stream comprising benzene, toluene, and xylene, and a residual stream comprising cracked naphtha, light cycle oil and heavy cycle oil In additional embodiments, one or more of the hydrogen fraction, the C1 stream, the C2 stream, the C3-C4 alkane stream, and the residual stream may be recycled as a feedstream to one or more of the unit operations within the integrated process for further processing.

In accordance with one or more embodiments of the present disclosure, an integrated system for conversion of crude oil to value added petrochemicals is disclosed. The system includes (i) a feed separator to separate a hydrocarbon stream comprising the crude oil into a light crude fraction boiling at a first temperature or less and a heavy crude fraction boiling at greater than the first temperature, wherein the first temperature is between 190 and 210° C.; (ii) a solvent deasphalting unit fluidly connected to the feed separator to receive the heavy crude fraction boiling at a temperature greater than the first temperature from the feed separator, wherein residue heavy components having a boiling point above 300° C. and asphaltenes are removed from the heavy crude fraction to generate a pitch product comprising the asphaltenes and residue heavy components and a deasphalted oil product; (iii) a delayed coker unit fluidly connected to the solvent deasphalting unit to receive the pitch product, wherein the pitch product undergoes thermal cracking reaction to obtain solid petroleum coke and a delayed coker product stream comprising C1-C4 light gases, coker naphtha, and coker gas oil; (iv) a hydrotreater fluidly connected to the feed separator, the solvent deasphalting unit, and the delayed coker to receive the light crude fraction boiling at the first temperature or less, the deasphalted oil product, and the delayed coker product stream, wherein the light crude fraction, the deasphalted oil product, and the delayed coker product stream are hydrotreated to remove heteroatoms and saturate carbon-carbon bonds to generate a hydrotreater product stream; (v) a first separator unit fluidly connected to the hydrotreater to receive the hydrotreater product stream, wherein the hydrotreater product stream is separated into a C1 fraction, a C2 fraction, a C3-C4 fraction, a hydrotreated light fraction comprising C5 hydrocarbons to hydrocarbons boiling at less than a second temperature, and a hydrotreated heavy fraction comprising hydrocarbons boiling at the second temperature or greater, (vi) a methane cracker fluidly connected to the first separator unit to receive the C1 fraction, wherein the C1 fraction is converted to a hydrogen stream and a fixed carbon stream; (vii) an ethane steam cracker fluidly connected to the first separator to receive the C2 fraction, wherein the C2 fraction is cracked to generate an ethane steam cracker product stream comprising light olefins and aromatics; (viii) a dehydrogenation reactor fluidly connected to the first separator to receive the C3-C4 fraction, wherein the C3-C4 fraction is dehydrogenated to generate a dehydrogenated product stream comprising propylene and butenes generated from propane and butanes in the C3-C4 fraction, (ix) an aromatization unit fluidly connected to the first separator to receive the hydrotreated light fraction, wherein the aromatization unit converts aliphatic hydrocarbons in the hydrotreated light fraction to aromatics to generate an aromatization product stream; (x) a steam enhanced catalytic cracking unit fluidly connected to the first separator to receive the hydrotreated heavy fraction comprising hydrocarbons boiling at the second temperature or greater, wherein the hydrotreated heavy fraction is cracked to generate a SECC product stream comprising light olefins; and (xi) a second separator fluidly connected to the ethane steam cracker, the dehydrogenation reactor, the aromatization unit, and the steam enhanced catalytic cracking unit to receive the ethane steam cracker product stream, the dehydrogenated product stream, the aromatization product stream, and the SECC product stream, wherein the second separator unit splits the ethane steam cracker product stream, dehydrogenated product stream, the aromatization product stream, and the SECC product stream into a hydrogen fraction, a C1 stream, a C2 stream, a C3-C4 alkane stream, a light olefin stream, a BTX stream comprising benzene, toluene, and xylene, and a residual stream comprising cracked naphtha, light cycle oil and heavy cycle oil.

In additional embodiments, one or more of the hydrogen fraction, the C1 stream, the C2 stream, the C3-C4 alkane stream, and the residual stream may be recycled as a feedstream to one or more of the unit operations within the integrated system for further processing.

Additional features and advantages of the described embodiments will be set forth in the detailed description that follows. The additional features and advantages of the described embodiments will be, in part, readily apparent to those skilled in the art from that description or recognized by practicing the described embodiments, including the detailed description that follows as well as the drawings and the claims.

BRIEF DESCRIPTION OF THE DRAWINGS

The following detailed description of specific embodiments of the present disclosure can be best understood when read in conjunction with the following drawings in which.

FIGURE (FIG.) 1 is a schematic illustration of one or more embodiments of the integrated refinery process of the present disclosure including an aromatization reactor.

Figure 1:
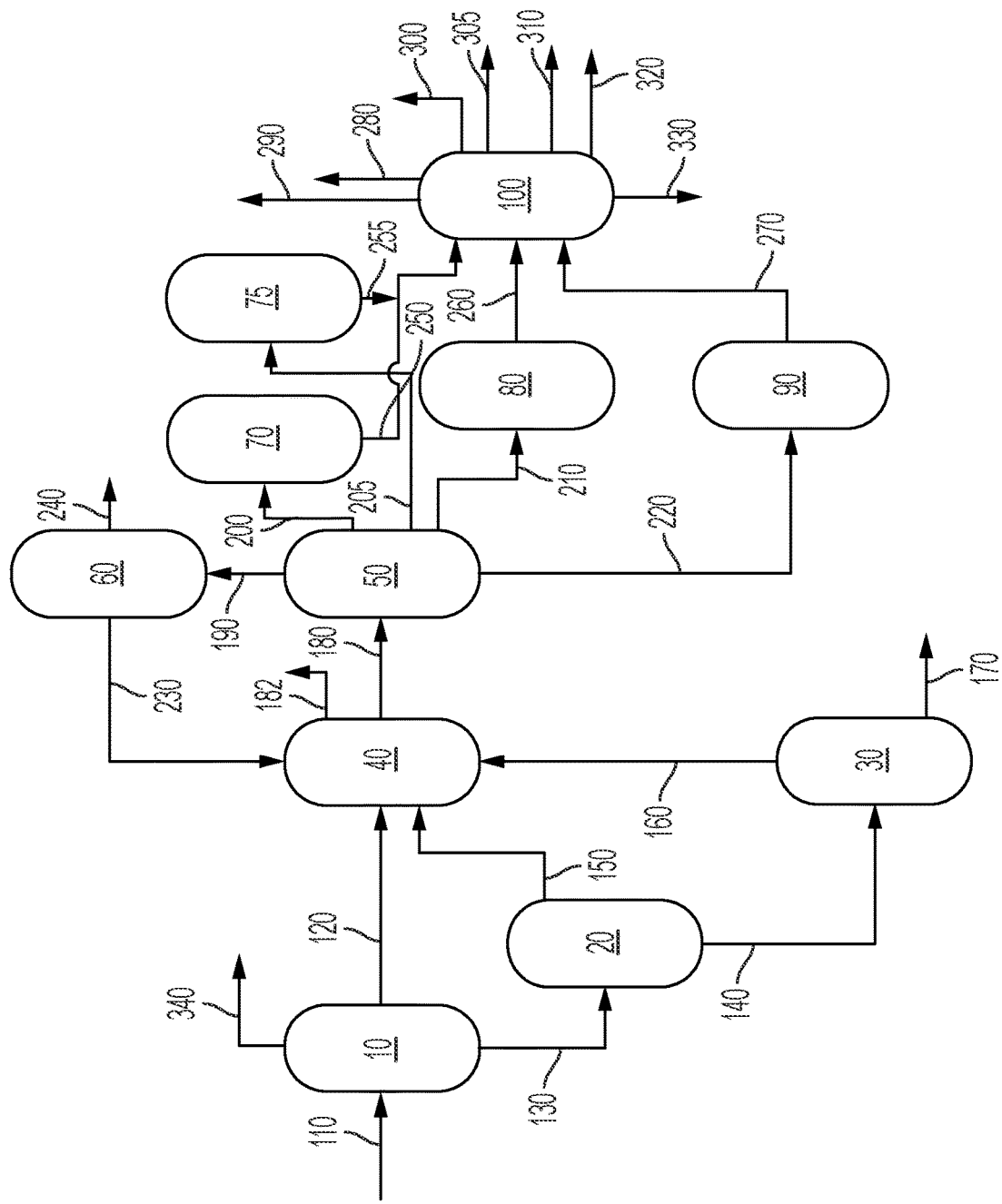

For the purpose of these simplified schematic illustrations and the present description, the numerous valves, temperature sensors, electronic controllers and the like that are customarily employed and well known to those of ordinary skill in the art of certain refinery operations are not included. Further, accompanying components that are in conventional refinery operations such as, for example, air supplies, hydrogen supplies, catalyst hoppers, and flue gas handling are not necessarily shown.

It should further be noted that arrows in the drawings refer to pipes, conduits, channels, or other physical transfer lines that connect by fluidic communication one or more system apparatuses to one or more other system apparatuses. Additionally, arrows that connect to system apparatuses define inlets and outlets in each given system apparatus.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Figure 2:
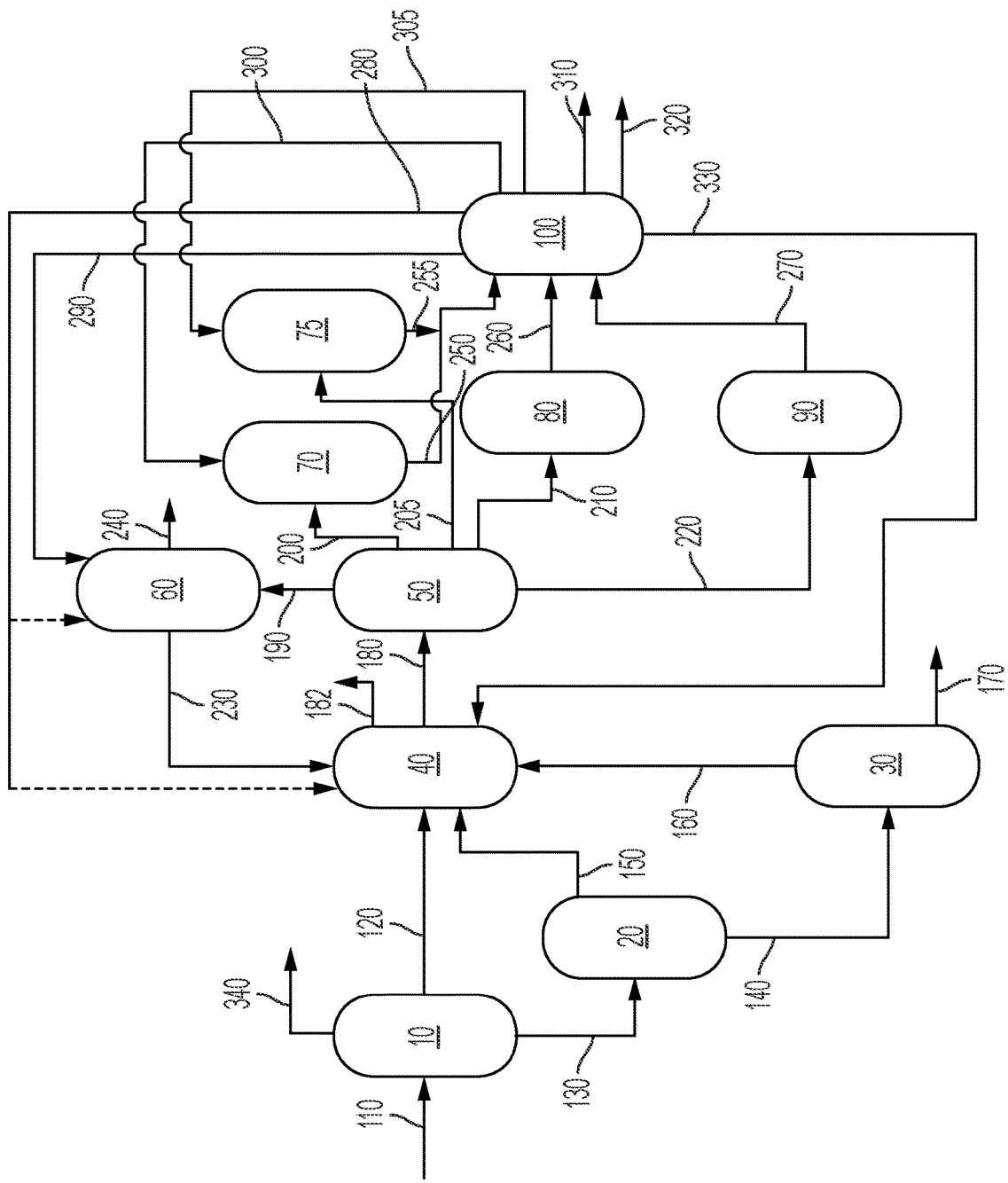
FIG. 2 is a schematic illustration of one or more embodiments of the integrated refinery process of the present disclosure including recycling of one or more product streams as additional feeds to one or more unit operations of the integrated refinery process.

Reference will now be made in detail to embodiments of an integrated process and associated system for conversion of crude oil to value added petrochemicals of the present disclosure. While the system for conversion of crude oil to value added petrochemicals of FIGS. 1 and 2 are provided as exemplary, it should be understood that the present systems and methods encompass other configurations.

The processes and systems of the present disclosure provide an integrated process and system for conversion of crude oil to enhanced value products, predominantly light olefins and BTX (benzene, toluene, and xylenes). Specifically, the processes and systems of the present disclosure split crude oil into a C1 fraction, a C2 fraction, a C3-C4 fraction, a light liquid fraction, and a heavy liquid fraction, which may then be cracked in the appropriate reactor such as a methane cracker, an ethane steam cracker, a dehydrogenation reactor, an aromatization unit, or a steam enhanced catalytic cracking unit to maximize the yield of petrochemicals. As such, the integrated system and processes yield improved production of light olefins and BTX.

In one or more embodiments, an integrated process for conversion of crude oil to value added petrochemicals includes providing a hydrocarbon stream 110 comprising the crude oil a feed separator 10 to separate the hydrocarbon stream 110 into a light crude fraction 120 boiling at a first temperature or less and a heavy crude fraction 130 boiling at a temperature greater than the first temperature, wherein the first temperature is between 190 and 210° C. The integrated process further comprises providing the heavy crude fraction 130 from the feed separator 10 to a solvent deasphalting unit 20, wherein residue heavy components having a boiling points above 300° C. and asphaltenes are removed from the heavy crude fraction to generate a pitch product 140 comprising the asphaltenes and residue heavy components and a deasphalted oil product 150. The pitch product 140 is then provided to a delayed coker unit 30, wherein the pitch product 140 undergoes thermal cracking reaction to obtain solid petroleum coke 170 and a delayed coker product stream 160 comprising C1-C4 light gases, coker naphtha, and coker gas oil. The light crude fraction 120, the deasphalted oil product 150, and the delayed coker product stream 160 are then provided to a hydrotreater 40, wherein the light crude fraction 120, the deasphalted oil product 150, and the delayed coker product stream 160 are hydrotreated to remove heteroatoms and saturate carbon-carbon bonds to generate a hydrotreater product stream 180. The hydrotreater product stream 180 is then provided to a first separator unit 50, wherein the hydrotreater product stream 180 is separated into a C1 fraction 190, a C2 fraction 200, a C3-C4 fraction 205, a hydrotreated light fraction 210 comprising C5 hydrocarbons to hydrocarbons boiling at less than a second temperature, and a hydrotreated heavy fraction 220 comprising hydrocarbons boiling at or greater than the second temperature, wherein the second temperature is between 200 and 215° C. The C1 fraction 190 is provided to a methane cracker 60, wherein the C1 fraction 190 is converted to a hydrogen stream 230 and a fixed carbon stream 240. The C2 fraction 200 is provided to an ethane steam cracker 70, wherein the C2 fraction 200 is cracked to generate an ethane steam cracker product stream 250 comprising light olefins and aromatics. The C3-C4 fraction 205 is provided to a dehydrogenation reactor 75, wherein the C3-C4 fraction 205 is dehydrogenated to generate a dehydrogenated product stream 255 comprising propylene and butenes generated from propane and butanes in the C3-C4 fraction 205. The hydrotreated light fraction 210 is provided to an aromatization unit 80, wherein the aromatization unit 80 converts aliphatic hydrocarbons in the hydrotreated light fraction 210 to aromatics to generate an aromatization product stream 260. The hydrotreated heavy fraction 220 comprising hydrocarbons boiling at the second temperature or greater is provided to a steam enhanced catalytic cracking unit 90, wherein the hydrotreated heavy fraction 220 is cracked to generate a SECC product stream 270 comprising light olefins. The ethane steam cracker product stream 250, the dehydrogenated product stream 255, the aromatization product stream 260, and the SECC product stream 270 are provided to a second separator unit 100, wherein the second separator unit 100 splits the ethane steam cracker product stream 250, the dehydrogenated product stream 255, the aromatization product stream 260, and the SECC product stream 270 into a hydrogen fraction 280, a C1 stream 290, a C2 stream 300, a C3-C4 alkane stream 305, a light olefin stream 310, a BTX stream 320 comprising benzene, toluene, and xylene, and a residual stream 330 comprising cracked naphtha, light cycle oil and heavy cycle oil.

In one or more embodiments, an integrated system for conversion of crude oil to value added petrochemicals includes a feed separator 10 to separate a hydrocarbon stream 110 comprising the crude oil into a light crude fraction 120 boiling at a first temperature or less and a heavy crude fraction 130 boiling at a temperature greater than the first temperature, wherein the first temperature is between 190 and 210° C. A solvent deasphalting unit 20 is fluidly connected to the feed separator 10 to receive the heavy crude fraction 130, wherein residue heavy components having a boiling point above 300° C. and asphaltenes are removed from the heavy crude fraction 130 to generate a pitch product 140 comprising the asphaltenes and residue heavy components and a deasphalted oil product 150. A delayed coker unit 30 is fluidly connected to the solvent deasphalting unit 20 to receive the pitch product 140, wherein the pitch product 140 undergoes a thermal cracking reaction to obtain solid petroleum coke 170 and a delayed coker product stream 160 comprising C1-C4 light gases, coker naphtha, and coker gas oil. A hydrotreater 40 is fluidly connected to the feed separator 10, the solvent deasphalting unit 20, and the delayed coker 30 to receive the light crude fraction 120 boiling at the first temperature or less, the deasphalted oil product 150, and the delayed coker product stream 160, wherein the light crude fraction 120, the deasphalted oil product 150, and the delayed coker product stream 160 are hydrotreated to remove heteroatoms and saturate carbon-carbon bonds to generate a hydrotreater product stream 180. A first separator unit 50 is fluidly connected to the hydrotreater 40 to receive the hydrotreater product stream 180, wherein the hydrotreater product stream 180 is separated into a C1 fraction 190, a C2 fraction, a C3-C4 fraction 205, a hydrotreated light fraction 210 comprising C5 hydrocarbons to hydrocarbons boiling at less than a second temperature, and a hydrotreated heavy fraction 220 comprising hydrocarbons boiling at the second temperature or greater, wherein the second temperature is between 200 and 215° C. A methane cracker 60 is fluidly connected to the first separator unit 50 to receive the C1 fraction 190, wherein the C1 fraction 190 is converted to a hydrogen stream 230 and a fixed carbon stream 240. An ethane steam cracker 70 is fluidly connected to the first separator 50 to receive the C2 fraction 200, wherein the C2 fraction 200 is cracked to generate an ethane steam cracker product stream 250 comprising light olefins and aromatics. A dehydrogentation reactor 75 is fluidly connected to the first separator 50 to receive the C3-C4 fraction 205, wherein the C3-C4 fraction 205 is dehydrogenated to generate a dehydrogenated product stream 255 comprising propylene and butenes generated from propane and butanes in the C3-C4 fraction 205. An aromatization unit 80 is fluidly connected to the first separator 50 to receive the hydrotreated light fraction 210, wherein the aromatization unit 80 converts aliphatic hydrocarbons in the hydrotreated light fraction 210 to aromatics to generate an aromatization product stream 260. A steam enhanced catalytic cracking unit 90 is fluidly connected to the first separator 50 to receive the hydrotreated heavy fraction 220 comprising hydrocarbons boiling at the second temperature or greater, wherein the hydrotreated heavy fraction 220 is cracked to generate a SECC product stream 270 comprising light olefins. A second separator 100 is fluidly connected to the ethane steam cracker 70, the dehydrogenation reactor 75, the aromatization unit 80, and the steam enhanced catalytic cracking unit 90 to receive the ethane steam cracker product stream 250, the dehydrogenated product stream 255, the aromatization product stream 260, and the SECC product stream 270, wherein the second separator unit 100 splits the steam cracker product stream 250, the aromatization product stream 260, and the SECC product stream 270 into a hydrogen fraction 280, a C1 stream 290, a C2 stream 300, a C3-C4 alkane stream 305, a light olefin stream 310, a BTX stream 320 comprising benzene, toluene, and xylene, and a residual stream 330 comprising cracked naphtha, light cycle oil and heavy cycle oil.

Having disclosed the basic operation of the integrated process and associated system for conversion of crude oil to value added petrochemicals, each step and unit operation of the embodiments of the integrated process and associated system are now provided in further detail.

Hydrocarbon Feed Stream

The hydrocarbon stream 110 comprises crude oil. In various embodiments, the crude oil in the hydrocarbon stream 110 may be Arab Extra Light crude oil (AXL), Arab Light crude oil (AL), Arab Heavy crude oil (AH), atmospheric resid, or combinations thereof.

Feed Separator

In one or more embodiments, the hydrocarbon stream 110 comprising the crude oil is provided to the feed separator 10 to separate the hydrocarbon stream 110 into the light crude fraction 120 boiling at a first temperature or less and the heavy crude fraction 130 boiling at a temperature greater than the first temperature. In various embodiments, the first temperature may be between 190 and 210° C., between 195 and 205° C., between 198 and 202° C., or approximately 200° C.

The feed separator 10 may be any unit configured to separate the hydrocarbon stream 110 into the light crude fraction 120 boiling at a temperature of 200° C. or less and the heavy crude fraction 130 boiling at a temperature greater than 200° C. In one or more embodiments, the feed separator 10 is a flash tank. A flash tank operates on the principle of flashing which refers to the process of liquid hydrocarbons immediately transitioning into vapor when moving from high to low pressure thereby allowing for separation of the feed of liquid hydrocarbons. The flash tank may operate at a temperature of 200 to 500° C. and appropriate pressure to enable separation into the light crude fraction 120 and the heavy crude fraction 130.

Solvent Deasphalting Unit

In one or more embodiments, the heavy crude fraction 130 boiling at greater than the first temperature from the feed separator 10 is provided to the solvent deasphalting unit 20. As such, and with reference to FIGS. 1 and 2, the solvent deasphalting unit 20 is fluidly connected to the feed separator 10. The solvent deasphalting unit 20 removes residue heavy components having a boiling point above 300° C. and asphaltenes from the heavy crude fraction 130 to generate the pitch product 140 comprising the asphaltenes and residue heavy components. The resulting stream generated from the removal of the asphaltenes and residue heavy components is the deasphalted oil product 150.

It will be appreciated that solvent deasphalting as performed in the solvent deasphalting unit 20 is a separation process in which certain species are selectively separated by molecular type by mixing with paraffinic solvents and precipitating out of solution the asphaltenes and other residue heavy components. The solvent deasphalting unit 20 separates the pitch product 140 comprising the asphaltenes and residue heavy components from the feedstock of the heavy crude fraction 130 because light hydrocarbons may act as solvents to dissolve aliphatic compounds but not asphaltenes.

In various embodiments, the solvent utilized in the solvent deasphalting unit 20 may be propane, butane, or pentane. The selection of light hydrocarbon solvent effects the yield and quality of the generated deasphalted oil product 150. For example, deasphalted oil product 150 generated using propane in the solvent deasphalting unit 20 may generate a deasphalted oil product 150 with a higher quality but lower yield compared with using pentane which may double or triple the yield at the expense of lower quality from greater residual contamination by metals and carbon residues.

Various processing parameters are considered suitable for the operation of the solvent deasphalting unit 20. For example, the solvent deasphalting unit 20 may operate at a temperature and a pressure less than the solvent critical pressure and temperature of the solvent utilized. Additionally, the yield of the pitch product 140 comprising the asphaltenes and residue heavy components and the deasphalted oil product 150 may be adjusted by varying the ratio of the solvent and the heavy crude fraction 130 provided to the solvent deasphalting unit 20. In one or more embodiments, the ratio by weight of the solvent to the heavy crude fraction 130 is from 2 to 20, or from 5 to 10, or from 6 to 8. Further, in one or more embodiments, the solvent deasphalting unit 20 is operated at a temperature ranging from 120° C. to 160° C. and a pressure ranging from 1 to 40 bar.

In one or more embodiments, the solvent deasphalting unit 20 additionally removes metals from the heavy crude fraction 130. The process of solvent deasphalting results in the metal containing hydrocarbons of the processed stream ending up with the asphaltenes and residue heavy components in the pitch product 140 of the solvent deasphalting unit 20. U.S. Pat. No. 7,566,394, incorporated by reference, teaches details of a solvent deasphalting process.

The deasphalting performed in the deasphalting unit 20 generates the deasphalted oil product 150 with many of the contaminants present in the heavy crude fraction 130 removed. A majority of the contaminants present in the heavy crude fraction 130 are removed as part of the pitch product 140. These contaminants include metal contaminants such Ni and V, and carbon residues.

Delayed Coker Unit

In one or more embodiments, the pitch product 140 from the solvent deasphalting unit 20 is provided to the delayed coker unit 30. As such, and with reference to FIGS. 1 and 2, the delayed coker unit 30 is fluidly connected to the solvent deasphalting unit 20. Within the delayed coker unit 30 the pitch product 140 undergoes a thermal cracking reaction to obtain the solid petroleum coke 170 and the delayed coker product stream 160. The delayed coker product stream 160 includes C1-C4 light gases, coker naphtha, and coker gas oil. Specifically, the delayed coker unit 30 operates by heating the pitch product 140 provided as a feed stream to its thermal cracking temperature in a furnace with multiple parallel passes. Such heating cracks the heavy, long chain hydrocarbon molecules of the pitch product 140 the solid petroleum coke 170 and the various components of the delayed coker product stream 160.

In one or more embodiments, the delayed coker product stream 160 is split into a first delayed coker product stream 162 and a second delayed coker product stream 164. The second delayed coker product stream 164 includes the C5 to hydrocarbons boiling at 343° C. from the delayed coker product stream 60 and the first delayed coker product stream 162 includes the remainder of the delayed coker product stream in the first delayed coker product stream.

In one or more embodiments, a coke drum in the delayed coker unit is operated at a temperature ranging from 470° C. to 505° C. and a pressure ranging from 1 to 2 bar to process the pitch product 140 from the solvent deasphalting unit 20.

The delayed coker unit 30 may include at least two parallel drums which are operated in a swing mode. When one coke drum is full of coke, the feed of the pitch product 140 is switched to a fresh empty drum, and the full drum is cooled. It will be appreciated that various inlet valves and outlet valves may be provided to control flow in and out of the delayed coker unit 30. The coke remaining in the drums is typically cooled with water and then removed from the coke drum by conventional methods, for example, using hydraulic or mechanical techniques, or both, to dislodge the solid coke from the drum walls for recovery as the solid petroleum coke 170.

Hydrotreater

In one or more embodiments, the light crude fraction 120 from the feed separator 10, the deasphalted oil product 150 from the solvent deasphalting unit 20, and the delayed coker product stream 160 from the delayed coker unit 30 are provided to the hydrotreater 40. As such, and with reference to FIGS. 1 and 2, the hydrotreater 40 is fluidly connected to the solvent deasphalting unit 20. In one or more embodiments and with reference to FIG. 3, the first delayed coker product stream 162 is provided in lieu of the delayed coker product stream 160 to the hydrotreater. Within the hydrotreater 40 the light crude fraction 120, the deasphalted oil product 150, and the delayed coker product stream 160 are hydrotreated to remove heteroatoms and saturate carbon-carbon bonds to generate the hydrotreater product stream 180. It will be appreciated that hydrotreating as performed in the hydrotreater 40 is the reaction of organic compounds in the presence of high pressure hydrogen to remove oxygen along with other heteroatoms such as nitrogen, sulfur, and chlorine through saturating the carbon-carbon bonds of the organic compounds in the feed stream.

Saturating the carbon-carbon bonds of the hydrocarbons in the light crude fraction 120, the deasphalted oil product 150, and the delayed coker product stream 160 removes heteroatoms such as nitrogen, sulfur, and chlorine by generating ammonia, hydrogen sulfide, and HCl respectively which may be separated out in a hydrotreater waste stream 182. In one or more embodiments, the hydrotreater product stream 180 exiting the hydrotreater 40 comprises less than 800 ppm nitrogen and less than 900 ppm sulfur. In various further embodiments, the hydrotreater product stream 180 comprises less than 750 ppm nitrogen, less than 650 ppm nitrogen, less than 550 ppm nitrogen, less than 500 ppm nitrogen, or 370 to 750 ppm nitrogen. In various embodiments, the hydrotreater product stream 180 comprises less than 850 ppm sulfur, less than 750 ppm sulfur, less than 500 ppm sulfur, less than 300 ppm sulfur, or 150 to 820 ppm sulfur.

Operation of the hydrotreater 40 includes mixing the feed stream of the light crude fraction 120, the deasphalted oil product 150, and the delayed coker product stream 160 with hydrogen gas, heating and pressurizing the resultant mixture, and passing the same over a catalyst to convert the sulfur containing compounds to hydrogen sulfide and desulfinated hydrocarbons, the nitrogen containing compounds to ammonia and denitrogenated hydrocarbons, and the chloride containing compounds to HCl and dechlorinated compounds. In one or more embodiments, the hydrotreater 40 may comprise a CoMo/alumina or NiMo/alumina catalyst.

In one or more embodiments, the hydrotreater 30 may operate at a temperature of 280 to 450° C. In one or more embodiments, the hydrotreater 30 may operate at a pressure of 5 to 160 bar with the introduction of hydrogen via a hydrogen inlet. In various further embodiments, the hydrotreater 40 may operate at a temperature of 280 to 425° C., 280 to 400° C., or 280 to 350° C. and a pressure of 5 to 100 bar, 5 to 50 bar, 20 to 160 bar, 20 to 100 bar or 20 to 50 bar. In one or more embodiments, the hydrotreater 30 may operate with a space velocity of the hydrocarbon of 1 to 10 h$^{-1}$.

First Separator Unit

In one or more embodiments, the hydrotreater product stream 180 from the hydrotreater 40 is provided to the first separator unit 50. As such, and with reference to FIGS. 1 and 2, the first separator unit 50 is fluidly connected to the hydrotreater 40. The first separator unit 50 splits the hydrotreater product stream 180 into the C1 fraction 190, the C2 fraction 200, the C3-C4 fraction 205, the hydrotreated light fraction 210 comprising C5 hydrocarbons to hydrocarbons boiling at less than a second temperature, and the hydrotreated heavy fraction 220 comprising hydrocarbons boiling at the second temperature or greater. In various embodiments, the second temperature may be between 200 and 215° C., between 200 and 210° C., between 204 and 210° C., approximately 204° C., or approximately 210° C.

The first separator unit 50 may comprise any unit operation or system known to those skilled in the art for separating a hydrocarbon stream by vapor pressure. An example first separator unit 50 is an atmospheric distillation unit. An atmospheric distillation unit utilizes fractional distillation by heating the feed to a temperature at which one or more fractions of the mixture will vaporize while leaving other fractions as liquid to separate the feed stream. Further, in various embodiments, the first separator unit 50 may be a simple flash column or true boiling point distillation with at least 15 theoretical plates.

In one or more embodiments, the first separator unit 50 comprises a plurality of separation units. For ease of illustration, the provided FIGS. 1 and 2 illustrate a single unit operation, but it will be appreciated that such unit operation may comprise multiple individual separator units to generate the disclosed product streams.

Methane Cracker

In one or more embodiments, the C1 fraction 190 from the first separator unit 50 is provided to the methane cracker 60. As such, and with reference to FIGS. 1 and 2, the methane cracker 60 is fluidly connected to the first separator unit 50. Within the methane cracker 60 the C1 fraction 190 is converted to the hydrogen stream 230 and the fixed carbon stream 240. Specifically, the methane cracker 60 operates by heating C1 fraction 190 provided as a feed stream from the first separator unit 50 to decompose the methane into hydrogen forming the hydrogen stream 230 and carbon forming the fixed carbon stream 240.

Methane cracking is an endothermic reaction that takes place at high temperatures and once the temperature reaches 300° C., methane theoretically starts to decompose into solid carbon particles and $H_2$ gas without any catalyst, according to thermodynamics. However, non-catalytic thermal decomposition of methane does not reach reasonable yields below approximately 1200° C. due to kinetic limitations and to the high activation energy required to break stable C—H bonds of methane molecules. As such, in one or more embodiments, a methane cracking catalyst is utilized in the methane cracker 60 to reduce the activation energy to break the C—H bonds. Catalytic methane decomposition achieves reasonable yields at a temperature as low as 700° C.

In various embodiments, the methane cracking catalyst utilized in the methane cracker 60 is is a nickel, cobalt, or iron based catalyst. Such catalysts are desirable due to their low cost and availability. Further, in one or more embodiments, supports and promoters may be added to the metal catalysts to enhance their catalytic performance. Typical supports used are $Al_2O_3$, MgO and $SiO_2$. In various embodiments, the methane cracking catalyst utilized in the methane cracker 60 is $Ni/CeO_2$, $NiLa_2O_3$, $Ni/SiO_2$, $Fe/CeO_2$, Fe/La$_2$O$_3$, Fe/SiO$_2$, Ni/SiO$_2$, Fe/SiO$_2$, Co/SiO$_2$, Ni/Mg—O—Al, Rh/Al$_2$O$_3$, or Rh/Al$_2$O$_3$–10 wt % Nd$_2$O$_3$.

In one or more embodiments, the methane cracker 60 is operated at a temperature ranging from 700° C. to 1,200° C. In further embodiments, the methane cracker 60 is operated at a temperature ranging from 700° C. to 1,000° C.

Ethane Steam Cracker

In one or more embodiments, the C2 fraction 200 from the first separator unit 50 is provided to the ethane steam cracker 70. As such, and with reference to FIGS. 1 and 2, the ethane steam cracker 70 is fluidly connected to the first separator unit 50. Within the ethane steam cracker 70 the C2 fraction 200 is cracked to generate an ethane steam cracker product stream 250 comprising light olefins and aromatics. Generally, steam cracking is a petrochemical process in which saturated hydrocarbons are broken down into smaller, often unsaturated, hydrocarbons. In operation, the C2 fraction 200 is diluted with steam and briefly heated in a furnace of the ethane steam cracker 70 in the absence of oxygen. The reaction occurs rapidly with a residence time on the order of milliseconds with the flow quickly quenched after reaching the cracking temperature to stop the cracking reaction. Specifically, the ethane steam cracker 70 operates by heating the C2 fraction 200 provided as a feed stream from the first separator unit 50 with steam to thermally crack the saturated hydrocarbons of the C2 fraction 200 into light olefins and primarily ethylene. For purposes of the present disclosure, light olefins are considered to be C2-C4 alkenes including ethylene, propylene, and butylene.

In one or more embodiments, the ethane steam cracker 70 is operated at a temperature ranging from 800° C. to 950° C. It will be appreciated that a greater cracking temperature, also referred to as severity, favors the production of shorter chain hydrocarbons as greater cracking occurs as compared to lower severity operation.

In one or more embodiments, the ethane steam cracker 70 is operated with a hydrocarbon to steam ratio in the range of 0.2 to 0.8. In one or more further embodiments, the ethane steam cracker 70 is operated with a hydrocarbon to steam ratio in the range of 0.2 to 0.5. It will be appreciated that the hydrocarbon to steam ratio represents the ratio of the hydrocarbons provided in the C2 fraction 200 from the first separator unit 50 to the steam concurrently provided to the ethane steam cracker 70.

Table 1, presented infra, provides generalized steam cracker yields generated based on the composition of the feed stream to the ethane steam cracker 70. Yields, as a weight percentage, are provided for ethane, the main consistent components of the C2 fraction 200 as well as for propane, butane, naphtha and gasoil which may be provided in the C2 fraction 200 in small quantities as a result of imperfection of separation in the first separator unit 50

TABLE 1

Theoretical Steam Cracker Yields For Various Feedstocks

| Yield by weight | Ethane (%) | Propane (%) | Butane (%) | Naphtha (%) | Gasoil (%) |
|---|---|---|---|---|---|
| Hydrogen and Methane | 13 | 28 | 24 | 26 | 18 |
| Ethylene | 80 | 45 | 37 | 30 | 25 |
| Propylene | 2 | 15 | 18 | 13 | 14 |
| Butadiene | 1 | 2 | 2 | 5 | 5 |
| Mixed butenes | 2 | 1 | 6 | 8 | 6 |
| C5+ | 2 | 9 | 13 | 8 | 7 |
| Benzene | 0 | 0 | 0 | 5 | 5 |
| Toluene | 0 | 0 | 0 | 4 | 3 |
| Fuel oil | 0 | 0 | 0 | 2 | 18 |

Dehydrogenation Reactor

In one or more embodiments, the C3-C4 fraction 205 is provided to the dehydrogenation reactor 75. As such, and with reference to FIGS. 1 and 2, the dehydrogenation reactor 75 is fluidly connected to the first separator unit 50. Within the dehydrogenation reactor 75 the C3-C4 fraction 205 is dehydrogenated to generate the dehydrogenated product stream 255 comprising propylene and butenes which are generated from propane and butanes in the C3-C4 fraction 205.

In one or more embodiments, the dehydrogenation reactor 75 has a dehydrogenation catalyst disposed therein to dehydrogenate the C3-C4 fraction 205 to generate the dehydrogenated product stream 255 comprising propylene and butenes. The catalytic bed reactor of the dehydrogenation reactor 75 may operate as a fixed bed reactor in one or more embodiments. In further embodiments, the catalytic bed reactor of the dehydrogenation reactor 75 may operate as a moving bed reactor.

The dehydrogenation catalyst may be selected to efficiently dehydrogenate the C3-C4 fraction 205 and generate propylene and butenes. In accordance with various embodiments, the dehydrogenation catalyst may be zeolitic type or a chlorinated alumina type, each containing noble metals such as Pt or Pd or combinations of noble metals. Further, in various embodiments, the catalyst may comprise an active phase metal carried on a support containing an ultra-stable (US) Y-type zeolite, a Beta zeolite, or a mordenite zeolite. In various disclosed embodiments, the zeolite is referenced as a USY zeolite but a Beta zeolite or mordenite zeolite may be substituted in such disclosed embodiments.

In one or more embodiments the dehydrogenation catalyst may comprise an active phase metal carried on a support containing an ultra-stable (US) Y-type zeolite, in which a portion of aluminum atoms of the framework of said USY zeolite thereof is substituted with one or more of zirconium, titanium and hafnium atoms. In one or more embodiments, the support is alumina which acts as a binder. In one or more embodiments, zeolite may comprise 5 to 80 wt. % of the total catalyst.

In one or more specific embodiments, the USY zeolite is framework modified to contain zirconium and titanium atoms in place a portion of the aluminum atoms of the framework of said USY zeolite. In one or more embodiments, the USY zeolite may comprise 1 to 5 wt. % of zirconium and titanium on a zeolite basis.

In various embodiments, the active phase metal carried on the support containing the USY zeolite may be selected from Ru, Rh, Pd, Ag, Os, Ir, Pt, and Au. In one or more embodiments, the active phase metal carried on the support containing the USY zeolite is Pt in particular. In one or more embodiments, the active phase metal may comprise 0.1 to 1.5 wt. % of the total catalyst.

In one or more embodiments and in accordance with the various configurations, the C3-C4 fraction 205 is provided to the dehydrogenation reactor 40 at a liquid space velocity (LHSV) of 1 to 10 h$^{-1}$. In various further embodiments, the C3-C4 fraction 205 is provided to the dehydrogenation reactor 40 at a LHSV of 1 to 15 h$^{-1}$, 1 to 10 h$^{-1}$, 2 to 15 h$^{-1}$, 3 to 10 h$^{-1}$, 3 to 8 h$^{-1}$, or approximately 5 h$^{-1}$.

In one or more embodiments and in accordance with the various configurations, the dehydrogenation reactor 75 may be operated at a reaction temperature of 575 to 620° C. In various embodiments, the dehydrogenation reactor 75 may be operated at a reaction temperature of 590 to 620° C., 600 to 620° C., 575 to 600° C., or approximately 575° C. It will be appreciated that as temperature decreases the reactivity decreases but as temperature increases coke formation also increases.

In one or more embodiments and in accordance with the various configurations, the dehydrogenation reactor 75 may be pressurized. Pressurization may be achieved with hydrogen. In various embodiments, the dehydrogenation reactor 75 is operated at a pressure of 1 to 5 bar, 1.5 to 5 bar, 2 to 5 bar, or approximately 3 bar.

Aromatization Unit

In one or more embodiments, the hydrotreated light fraction 210 comprising C5 hydrocarbons to hydrocarbons boiling at less than the second temperature is provided to the aromatization unit 80. As such, and with reference to FIGS. 1 and 2, the aromatization unit 80 is fluidly connected to the first separator unit 50. Within the aromatization unit 80 aliphatic hydrocarbons in the hydrotreated light fraction 210 are converted to aromatics to generate the aromatization product stream 260 via a process of dehydrogenation and dehydrocyclization. The aromatization unit 80 includes at least one aromatization reactor with an aromatization catalyst disposed therein operable to generate a liquid product stream with increased aromatics content in the form of the aromatization product stream 260.

In accordance with various embodiments, the aromatization catalyst may include a metal oxide component dispersed on the surfaces of a zeolite support. The metal oxide component may include one or more oxides of metal elements selected from groups 4 to 13 of the International Union of Pure and Applied Chemistry (IUPAC) periodic table, such as groups 8 to 13 of the IUPAC periodic table. In one or more embodiments, the metal element of the one or more metal oxides may be a metal element selected from groups 4 to 13 and periods 4 to 6 of the IUPAC periodic table, such as period 4 of the periodic table. The metal element of the metal oxide may include, but is not limited to, titanium, vanadium, chromium, manganese, iron, cobalt, nickel, copper, zinc, gallium, molybdenum, palladium, silver, hafnium, tungsten, platinum, gold, or combinations of these metal elements. In one or more embodiments, the metal element of the one or more metal oxides may include gallium, zinc, iron, hafnium, or combinations of these metals. In one or more embodiments, the metal oxide may be gallium oxide.

In one or more embodiments the aromatization catalyst may comprise a gallium modified H-MFI type zeolite. Specifically, the aromatization catalyst may comprise a catalyst formed from gallium incorporated into a H-MFI type zeolite. Such a catalyst may comprise from 1 to 5 weight percent gallium (Ga) based on the total catalyst. For example, in various embodiments, the gallium modified H-MFI type zeolite catalyst may comprise from 1 to 4 weight percent gallium, 1 to 3 weight percent gallium, 1.5 to 2.5 weight percent gallium, 1.8 to 2.2 weight percent gallium, or approximately 2 weight percent gallium. It will be appreciated that integration of gallium at other ratios encompassed by the broadest ranges are also envisioned but not explicitly delineated for brevity. As previously indicted, in various embodiments, the gallium may be substituted with an alternative metal element while maintaining the remaining parameters of the disclosed gallium modified H-MFI type zeolite. In various embodiments, the silica to alumina ratio of the H-MFI type zeolite may vary from 20 to 100, 20 to 80, 20 to 50, or 20 to 30.

In one or more embodiments, the hydrotreated light fraction 210 from the first separator unit 50 is provided to the aromatization unit 80 at a liquid space velocity (LHSV) of 0.1 to 10 $h^{-1}$. In various further embodiments, the hydrotreated light fraction 210 is provided to the aromatization unit 80 at a LHSV of 0.1 to 8 $h^{-1}$, 0.3 to 10 $h^{-1}$, 0.5 to 5 $h^{-1}$, 0.8 to 3 $h^{-1}$, 0.8 to 2 $h^{-1}$, or approximately 1 $h^{-1}$. It will be appreciated that greater LHSV results in lower aromatics yield while lesser LHSV favors formation of less desirable heavy aromatics.

In one or more embodiments, the aromatization unit 80 may be operated at a reaction temperature of 400 to 600° C. In various embodiments, the aromatization unit 80 may be operated at a reaction temperature of 400 to 550° C., 425 to 550° C., 450 to 600° C., or 450 to 550° C. It will be appreciated that lesser temperature leads to lesser conversion while greater temperature results in faster catalyst deactivation.

In one or more embodiments, the aromatization unit 80 may be operated at a pressure of 1 to 35 bar, 5 to 35 bar, or 10 to 35 bar. It will be appreciated that lesser pressure favors aromatization reaction, but a minimum level of positive pressure is needed for practical operation.

Steam Enhanced Catalytic Cracking Unit

In one or more embodiments, the hydrotreated heavy fraction 220 from the first separator unit 50 comprising hydrocarbons boiling at or greater than the second temperature is provided to the steam enhanced catalytic cracking unit 90. As such, and with reference to FIGS. 1 and 2, the steam enhanced catalytic cracking unit 90 is fluidly connected to the first separator unit 50. Within the steam enhanced catalytic cracking unit 90 the hydrotreated heavy fraction 220 is cracked to generate the SECC product stream 270 comprising light olefins. In one or more embodiments, the deasphalted oil product 150, the second delayed coker product stream 164, or both are additionally provided to the steam enhanced catalytic cracking unit 90 to generate a combined SECC feedstream 222. As such, and with reference to FIG. 3, the steam enhanced catalytic cracking unit 90 may be fluidly connected to the solvent deasphalting unit 20, the delayed coker 30, or both.

Catalytic cracking is an understood conversion processes used in petroleum refineries and is utilized to convert the high-boiling, high-molecular weight hydrocarbon fractions of petroleum crude oils or other hydrocarbon stream into more valuable gasoline, olefinic gases, and other products. Similarly, steam cracking is an understood conversion processes used in petroleum refineries where a gaseous or liquid hydrocarbon feed such as naphtha diluted with steam and briefly heated in a furnace in the absence of oxygen to crack saturated hydrocarbons into smaller, often unsaturated, hydrocarbons such as olefins. The processing in accordance with the present disclosure is steam enhanced catalytic cracking which combines the benefits of both catalytic cracking and steam cracking to maximize the production of light olefins. Specifically, it is noted that the steam enhanced catalytic cracking unit 90 differs from conventional fluidized catalytic cracking reactors in that they operate at a higher temperature range and also include more steam content in the feed. The excessive steam and higher temperatures convert the feed hydrocarbons of the hydrotreated heavy fraction 220 into comparatively more light olefins such as ethylene and propylene. It is specifically noted that the steam enhanced catalytic cracking process performed in the steam enhanced catalytic cracking unit 90 allows heavy stream, such the hydrotreated heavy fraction 220, to be effectively cracked into light olefins.

The steam enhanced catalytic cracking unit 90 may operate as a fluidized bed reactor, a fixed bed reactor, or a moving bed reactor. In one or more particular embodiments, the steam enhanced catalytic cracking unit 90 may comprises a fluidized bed reactor in the form of a riser reactor or a downer reactor to convert the hydrotreated heavy fraction 220 to the SECC product stream 270 comprising light olefins having a carbon number of C2-C4. As used herein, the term "downer" refers to a catalytic cracking reactor, such as a fluidized bed reactor, where the reactant flows in a generally downward direction such as, for example, entering the top and exiting the bottom of the reactor. Likewise, the term "riser" refers to a catalytic cracking reactor, such as a fluidized bed reactor, where the reactant flows in a generally upward direction such as, for example, entering the bottom and exiting the top of the reactor.

In one or more embodiments, as the steam enhanced catalytic cracking unit 90 utilizes a steam enhanced cracking catalyst the steam enhanced catalytic cracking unit 90 may include a reactor/separator as well as a regeneration vessel for regenerating spent catalyst. As used herein, "spent catalyst" refers to catalyst which has undergone reaction with fuel and is at least partially coked. Also, as used herein, "regenerated catalyst" refers to catalyst that is exiting the catalyst regenerator and is at least partially or substantially free of coke, and "fresh catalyst" refers to catalyst that is newly entering the system and is at least partially or substantially free of coke. The hydrotreated heavy fraction 220 is admixed and intimately contacted with an effective quantity of heated fresh or regenerated steam enhanced cracking catalyst particles which catalytically crack hydrocarbon molecules within the hydrotreated heavy fraction 220 by carbon-carbon bond cleavage. The SECC product stream 270 and the steam enhanced cracking catalyst are separated with the steam enhanced cracking catalyst cycled to the regeneration vessel for regeneration of the steam enhanced cracking catalyst.

In general, the operating conditions for the steam enhanced catalytic cracking unit 90 in a configuration as a downer or a riser FCC unit include: a reaction temperature of from about 600° C. to about 750° C., in certain embodiments about 625° C. to about 725° C., and in further embodiments about 650° C. to about 700° C.; reaction pressure of from about 1 bar to about 20 bar, in certain embodiments about 1 bar to about 10 bar, and in further embodiments from about 1 bar to about 2 bar; contact time in the reactor of from about 0.1 seconds to about 30 seconds, in certain embodiments about 0.1 seconds to about 20 seconds, and in further embodiments about 0.1 seconds to about 10 seconds; a catalyst-to-feed ratio on a weight basis of from about 3:1 to about 60:1, in certain embodiments about 4:1 to about 50:1, and in further embodiments about 6:1 to about 40:1; and a steam-to-feed ratio on a weight basis of from about 1:5 to about 1:1, in certain embodiments about 1:4 to about 1:1, and in further embodiments about 1:4 to about 2:3. It is noted that the flow rate of the catalyst entering the steam enhanced catalytic cracking unit 90 divided by the flow rate of the hydrotreated heavy fraction 220 entering the steam enhanced catalytic cracking unit 90 defines the catalyst-to-feed ratio and the flow rate steam entering the steam enhanced catalytic cracking unit 90 divided by the flow rate of the hydrotreated heavy fraction 220 entering the steam enhanced catalytic cracking unit 90 defines the steam-to-feed ratio.

In various embodiments, the steam enhanced cracking catalyst provided in the steam enhanced catalytic cracking unit 90 may be a fluid catalytic cracking catalyst based on USY, zeolite beta, or ZSM-5. In one or more specific embodiments, the steam enhanced cracking catalyst provided in the steam enhanced catalytic cracking unit 90 may be a ZSM-5 formulated catalyst selected for high hydrothermal stability.

Second Separator Unit

In one or more embodiments, the ethane steam cracker product stream 250, the dehydrogenated product stream 255, the aromatization product stream 260, and the SECC product stream 270 are provided to the second separator unit 100. As such, and with reference to FIGS. 1 and 2, the second separator unit 100 is fluidly connected to the ethane steam cracker 70, the dehydrogenation reactor 75, the aromatization unit 80, and the steam enhanced catalytic cracking unit 90. The second separator unit 100 splits the ethane steam cracker product stream 250, the dehydrogenated product stream 255, the aromatization product stream 260, and the SECC product stream 270 into the hydrogen fraction 280, the C1 stream 290, the C2 stream 300, the C3-C4 alkane stream 305, the light olefin stream 310, the BTX stream 320 comprising benzene, toluene, and xylene, and the residual stream 330 comprising cracked naphlha, light cycle oil and heavy cycle oil.

The second separator unit 100 may comprise any unit operation or system known to those skilled in the art for separating a hydrocarbon stream by vapor pressure. An example second separator unit 100 is an atmospheric distillation unit. As previously noted, an atmospheric distillation unit utilizes fractional distillation by heating the feed to a temperature at which one or more fractions of the mixture will vaporize while leaving other fractions as liquid to separate the feed stream. Further, in various embodiments, the second separator unit 100 may be a simple flash column or true boiling point distillation with at least 15 theoretical plates.

In one or more embodiments, the second separator unit 100 comprises a plurality of separation units. For ease of illustration, the provided FIGS. illustrate a single unit operation, but it will be appreciated that such unit operation may comprise multiple individual separator units to generate the disclosed product streams.

Further Processing

In one or more embodiments and with reference to FIG. 2, the hydrogen stream 230 from the methane cracker 60 is provided to the hydrotreater 40. Further, in one or more embodiments, the hydrogen fraction 280 from the second separator unit 100 is provided to the hydrotreater 40. As such, and with reference to FIG. 2, the hydrotreater 40 may be fluidly connected to the methane cracker 60. It will be appreciated that recycling the generated hydrogen gas from the methane cracker 60, the second separator unit 100, or other unit operation within the integrated system to the hydrotreater 40 reduces the demand for make-up hydrogen gas provided from outside the integrated process to operate the hydrotreater 40.

In one or more embodiments and with reference to FIG. 2, the C1 stream 290 from the second separator unit 100 is recycled to the methane cracker 60 for further methane cracking. As previously indicated, cracking methane in the methane cracker 60 generates hydrogen gas which may beneficially be provided to the hydrotreater 40 to augment and reduce the demand from any external hydrogen source to operate the hydrotreater 40. Further, in one or more embodiments, the hydrogen fraction 280 from the second separator unit 100 is provided to the methane cracker 60 as well. It will be appreciated that providing both the hydrogen fraction 280 and the C1 stream 290 from the second separator unit 40 to the methane cracker 60 allows for the hydrogen fraction 280 and the C1 stream 290 to be provided as a single combined stream reducing the separation demand and complexity of the second separator unit 40. Any hydrogen gas provided to the methane cracker 90 may simply be exhausted as part of the hydrogen stream 230 from the methane cracker 60 is provided to the hydrotreater 40. As such, and with reference to FIG. 2, the methane cracker 60, the hydrotreater 40, or both may be fluidly connected to the second separator unit 100.

In one or more embodiments, in lieu of providing the hydrogen stream 230 from the methane cracker 60, the hydrogen fraction 280 from the second separator unit 100, or both to hydrotreater 40, one or both of the hydrogen stream 230 and the hydrogen fraction 280 may be collected or provided for utilization in a fuel cell vehicle. Similarly, the hydrogen from one or both of the hydrogen stream 230 and the hydrogen fraction 280 may be provided to a fuel cell for generation of heat and electricity.

In one or more embodiments and with reference to FIG. 2, the C2 stream 300 from the second separator unit 100 is recycled to the ethane steam cracker 70 for further conversion to light olefins and more particularly ethylene. As such, and with reference to FIG. 2, the ethane steam cracker 70 may be fluidly connected to the second separator unit 100.

In one or more embodiments and with reference to FIG. 2, the C3-C4 alkane stream 305 from the second separator unit 100 is recycled to the dehydrogenation reactor 75 for further conversion to for further conversion to propylene and butenes. As such, and with reference to FIG. 2, the dehydrogenation reactor 75 may be fluidly connected to the second separator unit 100.

In one or more embodiments and with reference to FIG. 2, the residual stream 330 comprising cracked naphtha, light cycle oil and heavy cycle oil from the second separator unit 100 is recycled to the hydrotreater 40 for further processing. As such, and with reference to FIG. 2, the hydrotreater 40 may be fluidly connected to the second separator unit 100.

In one or more embodiments the feed separator 10 may additionally generate an off-gas stream 340 comprising C1-C4 gases. The off-gas stream 340 may be separated in any unit operation or system known to those skilled in the art for separating a hydrocarbon stream by vapor pressure or other parameter to provide a stream of methane to pass to the methane cracker 60, a stream of C2 gases to pass to the ethane steam cracker 70, and a stream of C3-C4 gases to pass to the dehydrogenation reactor 75.

EXAMPLES

The following examples illustrate features of the present disclosure but are not intended to limit the scope of the disclosure.

Figure 3:
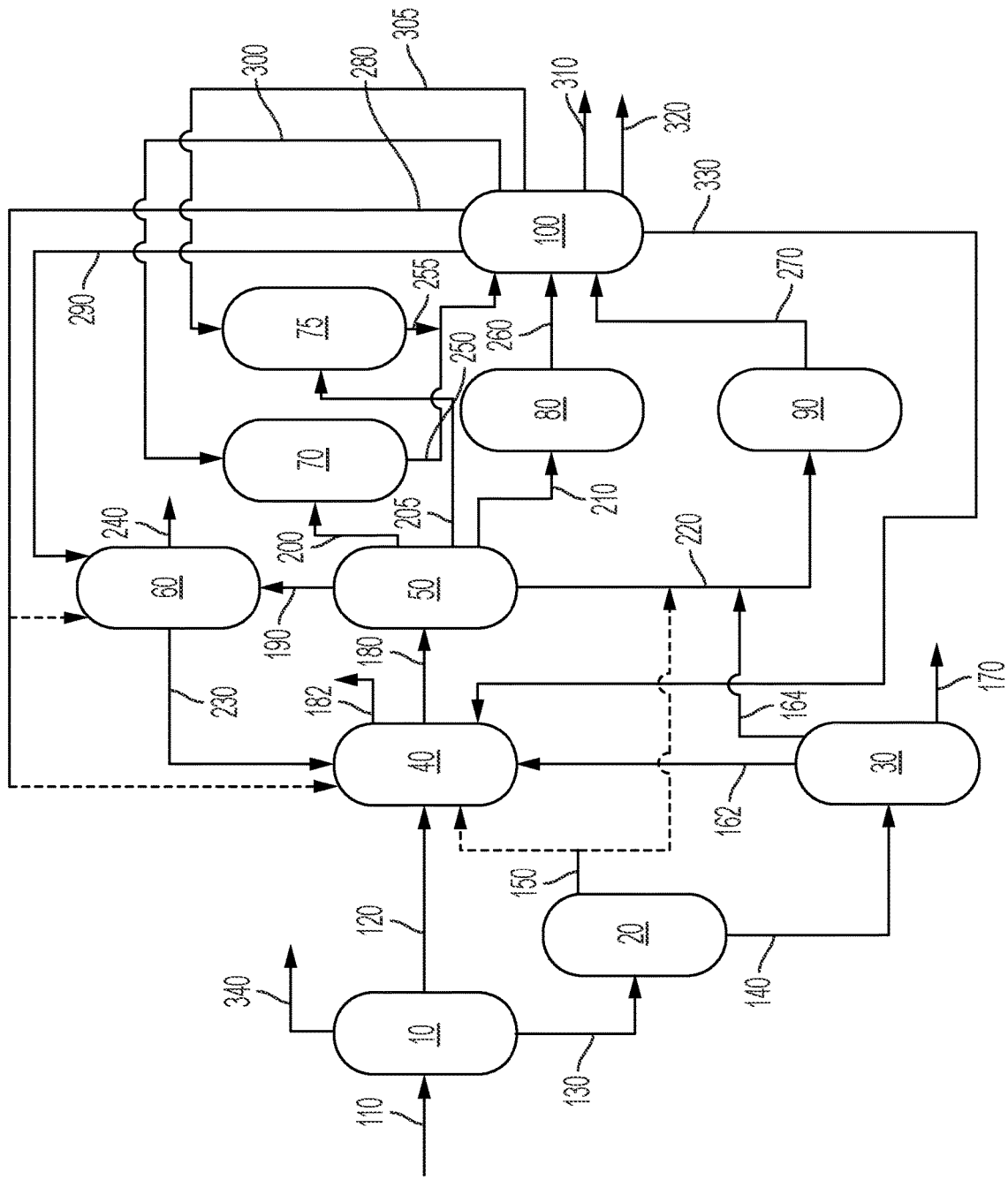
FIG. 3 is a schematic illustration of the integrated refinery process of FIG. 2 with optional additional stream splitting to separate unit operations.

To demonstrate the predominant production of value added petrochemicals, such as benzene, toluene, xylenes, and light olefins with processes and systems in accordance with the present disclosure, simulated yields form various processing units within the integrated process were calculated. It will be appreciated that laboratory scale operation of the complex and multi-unit nature of the integrated process would be impractical and that the computer simulation of the same provides a reasonable representation of full scale industrial implementation. The integrated process as illustrated in FIG. 3 was simulated to develop the Inventive Example.

The hydrocarbon stream 110 utilized for the Inventive Example was Arab Extra Light (AXL) crude oil with a composition as detailed in Table 2.

TABLE 2

Inventive Example Hydrocarbon Feed Stream (AXL)

| PARAMETER | VALUE |
|---|---|
| API[Petrol] | 40.4 |
| SG (60/60)[Petrol] | 0.8 |
| Std. Liquid Density[Petrol] [kg/m3] | 822.3 |
| TBP 0%[Petrol] [C] | −11.9 |
| TBP 5%[Petrol] [C] | 31.6 |
| TBP 10%[Petrol] [C] | 70.3 |
| TBP 30%[Petrol] [C] | 160.5 |
| TBP 50%[Petrol] [C] | 254.2 |
| TBP 70%[Petrol] [C] | 363.5 |
| TBP 90%[Petrol] [C] | 531.9 |
| TBP 95%[Petrol] [C] | 623.7 |
| TBP 100%[Petrol] [C] | 855.7 |

The hydrocarbon stream 110 was provided to a feed separator 10 to generate the light crude fraction 120 and the heavy crude fraction 130. Additionally an off-gas stream 340 was generated. The light crude fraction 120 comprises AXL-Naphtha representing the hydrocarbons boiling at 200° C. or less and the heavy crude fraction 130 comprises AXL-Heavy representing the hydrocarbons boiling at greater than 200° C. The off-gas stream 340 comprises C1-C4 gases. The breakdown of the product yields from the feed separator are provided in Table 3.

TABLE 3

Feed Separator Product Yields

| Component | Weight (%) |
|---|---|
| Off-gas | 2.4 |
| light crude fraction [AXL-Naphtha (200° C.−)] | 32.5 |
| heavy crude fraction [AXL-Heavy (200° C.+)] | 65.0 |

The heavy crude fraction 130 was provided to a solvent deasphalting unit 20. The yield of the deasphalting unit 20 was 94.1 wt. % deasphalted oil product 150 (DAO) and 5.9 wt. % pitch product 140.

The generated pitch product 140 was provided to a delayed coker 30 to generate the solid petroleum coke 170, the first delayed coker product stream 162, and the second delayed coker product stream 164. The second delayed coker product stream 164 includes C5 to 343° C. boiling range hydrocarbons and the first delayed coker product stream 162 includes the remainder of the components. The breakdown of the product yields from the delayed coker 30 in the first delayed coker product stream 162 and the second delayed coker product stream 164 are provided in Table 4. The fuel gas represents light gases less than C2, inclusive. The liquefied petroleum gas represents C3 and C4 light gases including both olefins and paraffins. The split between fuel gas and liquefied petroleum gas was at 15° C. It is noted that the generated solid petroleum coke 160 is omitted from the product yields.

TABLE 4

Delayed Coker Product Yields

| Component | Weight (%) |
|---|---|
| Fuel gas (FG) | 10.9 |
| Liquefied petroleum gas (LPG) | 6.1 |
| C5 to 350 F. (176.7° C.) Hydrocarbons | 18.4 |

TABLE 4-continued

Delayed Coker Product Yields

| Component | Weight (%) |
|---|---|
| 350 F. (176.7° C.) to 650 F. (343.3° C.) Hydrocarbons | 25.1 |
| 650 F. + (343.3° C.+) Hydrocarbons | 39.4 |

The light crude fraction 120 and the delayed coker product stream 160 were provided to a hydrotreater 40 to generate the hydrotreater product stream 180. The breakdown of the product yields from the hydrotreater 40 are provided in Table 5.

TABLE 5

Hydrotreater Product Yields

| Component | Weight (%) | |
|---|---|---|
| C1 and C$_2$ | 1.7 | methane, ethane, hydrogen |
| Liquefied petroleum gas (LPG) | 0.1 | propane, butane |
| Naphtha | 28.9 | C5, C6-221° C. |
| Distillate | 37.0 | 221-371° C. |
| Gas Oil | 30.9 | 371° C.-538° C. |
| Heavy Cycle Oil | 1.4 | 538° C.+ |

The hydrotreater product stream 180 was passed through a first separator unit 50 to generate the C1 fraction 190, the C2 fraction 200, the C3-C4 fraction 205, the hydrotreated light fraction 210 comprising C5 hydrocarbons to hydrocarbons boiling at less than 200° C., and the hydrotreated heavy fraction 220 comprising hydrocarbons boiling at 200° C. or greater.

The C1 fraction 190 was provided to a methane cracker 60 to generate the hydrogen stream 230 and the fixed carbon stream 240. The breakdown of the product yields from the methane cracker 60 are provided in Table 6.

TABLE 6

Methane Cracker Product Yields

| Component | Weight (%) |
|---|---|
| H$_2$ | 25.0 |
| Carbon | 75.0 |

The C2 fraction 200 was provided to an ethane steam cracker 70 to generate the ethane steam cracker product stream 250 comprising primarily light olefins. The C3-C4 fraction 205 was provided to a dehydrogenation reactor 75 to generate the dehydrogenated product stream 255 comprising propylene and butenes generated from propane and butanes in the C3-C4 fraction 205. The breakdown of the product yields for the combined stream formed from the ethane steam cracker product stream 250 and the dehydrogenated product stream 255 are provided in Table 7.

TABLE 7

Ethane Steam Cracker and Dehydrogenation Reactor Product Yields

| Component | Weight (%) |
|---|---|
| C1 and H$_2$ | 18.56 |
| Ethylene | 57.52 |
| Propylene | 9.63 |
| Butadiene | 2.74 |

TABLE 7-continued

Ethane Steam Cracker and Dehydrogenation Reactor Product Yields

| Component | Weight (%) |
|---|---|
| C5+ | 8.24 |
| Benzene | 2.17 |
| Toluene | 0.39 |
| Fuel Oil | 0.76 |

The hydrotreated light fraction 210 was provided to an aromatization unit 80 to generate the aromatization product stream 260. The breakdown of the product yields from the aromatization unit 80 are provided in Table 8.

TABLE 8

Aromatization Unit Product Yields

| Component | Weight (%) |
|---|---|
| C1 and H$_2$ | 5.0 |
| C2-C5 | 10.0 |
| Benzene | 2.0 |
| Toluene | 15.0 |
| Xylenes | 28.0 |
| C9, C10 aromatics | 25.0 |

The hydrotreated heavy fraction 220 and the deasphalted oil product 150 were provided to a steam enhanced catalytic cracking unit 90 to generate the SECC product stream 270 comprising light olefins. The breakdown of the product yields from the steam enhanced catalytic cracking unit 90 are provided in Table 9.

TABLE 9

Steam Enhanced Catalytic Cracking Unit Product Yields

| Component | Weight (%) | |
|---|---|---|
| C1 and H$_2$ | 3.0 | |
| C2-C4 alkanes | 9.2 | |
| C2-C4 alkenes | 41.0 | |
| Gasoline | 27.6 | C5-221° C. |
| Light Cycle Oil (LCO) | 8.0 | 221° C.-343° C. |
| Heavy Cycle Oil (HCO) | 5.9 | 343° C.+ |
| Coke | 5.2 | |

The ethane steam cracker product stream 250, the dehydrogenated product stream 255, the aromatization product stream 260, and the SECC product stream 270 were provided to a second separation unit 100 to generate various product streams. The hydrogen and C1 hydrocarbons from the second separation unit 100 were recycled back as a feed stream to the methane cracker 60 to for methane cracking and H$_2$ recovery. The C2 hydrocarbons from the second separation unit 100 were recycled back as a feed stream to the ethane steam cracker 70 for further conversion to light olefins. The C3-C4 alkanes were recycled back as a feed stream to the dehydrogenation reactor 75 for further conversion to propane and butanes. A residual stream comprising cracked naphtha, light cycle oil and heavy cycle oil was recycled back as a feed stream to the hydrotreater 40 for further processing therein and in the downstream unit operations. Further, a light olefin stream and a BTX stream comprising benzene, toluene, and xylene were collected as desirable value added petrochemicals as product streams from the second separation unit 100. The breakdown of the product yields from the overall system are provided in Table 10. The "other" includes bottom products such as light cycle oil and heavy cycle oil.

TABLE 10

Overall Product Yields

| Component | Weight (%) |
| --- | --- |
| H$_2$ | 2.5 |
| Fixed Carbon | 3.2 |
| Light Olefins | |
| Ethylene | 8.1 |
| Propene | 21.0 |
| Butenes | 13.7 |
| Total Light Olefins | 42.8 |
| BTX | |
| Butane, Toluene, Xylenes | 24.9 |
| C9+ | 13.8 |
| Other | 12.8 |

It is noted that the Inventive Example demonstrates that value added petrochemicals in the form of BTX and light olefins are the primary product generated from the integrated process and system. Specifically, the generated products are 42.8 wt. % light olefins and 24.9 wt. % BTX which together account for over 65 wt. % of the products.

It should now be understood the various aspects of the integrated process and system for conversion of crude oil to value added petrochemicals are described and such aspects may be utilized in conjunction with various other aspects.

According to a first aspect, an integrated process for conversion of crude oil to value added petrochemicals includes (i) providing a hydrocarbon stream comprising the crude oil to a feed separator to separate the hydrocarbon stream into a light crude fraction boiling at a first temperature or less and a heavy crude fraction boiling at greater than the first temperature, wherein the first temperature is between 190 and 210° C.; (ii) providing the heavy crude fraction boiling at a temperature greater than the first temperature from the feed separator to a solvent deasphalting unit, wherein residue heavy components having a boiling points above 300° C. and asphaltenes are removed from the heavy crude fraction to generate a pitch product comprising the asphaltenes and residue heavy components and a deasphalted oil product; (iii) providing the pitch product to a delayed coker unit, wherein the pitch product undergoes a thermal cracking reaction to obtain solid petroleum coke and a delayed coker product stream comprising C1-C4 light gases, coker naphtha, and coker gas oil; (iv) providing the light crude fraction boiling at the first temperature or less, the deasphalted oil product, and the delayed coker product stream to a hydrotreater, wherein the light crude fraction, the deasphalted oil product, and the delayed coker product stream are hydrotreated to remove heteroatoms and saturate carbon-carbon bonds to generate a hydrotreater product stream; (v) providing the hydrotreater product stream to a first separator unit, wherein the hydrotreater product stream is separated into a C1 fraction, a C2 fraction, a C3-C4 fraction, a hydrotreated light fraction comprising C5 hydrocarbons to hydrocarbons boiling at than a second temperature, and a hydrotreated heavy fraction comprising hydrocarbons boiling at or greater than the second temperature, wherein the second temperature is between 200 and 215° C.; (vi) providing the C1 fraction to a methane cracker, wherein the C1 fraction is converted to a hydrogen stream and a fixed carbon stream; (vii) providing the C2 fraction to an ethane steam cracker, wherein the C2 fraction is cracked to generate an ethane steam cracker product stream comprising light olefins and aromatics; (viii) providing the C3-C4 fraction to a dehydrogenation reactor, wherein the C3-C4 fraction is dehydrogenated to generate a dehydrogenated product stream comprising propylene and butenes generated from propane and butanes in the C3-C4 fraction; (ix) providing the hydrotreated light fraction comprising C5 hydrocarbons to hydrocarbons boiling at less than the second temperature to an aromatization unit, wherein the aromatization unit converts aliphatic hydrocarbons in the hydrotreated light fraction to aromatics to generate an aromatization product stream; (x) providing the hydrotreated heavy fraction comprising hydrocarbons boiling at the second temperature or greater to a steam enhanced catalytic cracking unit, wherein the hydrotreated heavy fraction is cracked to generate a SECC product stream comprising light olefins; and (xi) providing the ethane steam cracker product stream, the dehydrogenated product stream, the aromatization product stream, and the SECC product stream to a second separator unit, wherein the second separator unit splits the ethane steam cracker product stream, the dehydrogenated product stream, the aromatization product stream, and the SECC product stream into a hydrogen fraction, a C1 stream, a C2 stream, a C3-C4 alkane stream, a light olefin stream, a BTX stream comprising benzene, toluene, and xylene, and a residual stream comprising cracked naphtha, light cycle oil and heavy cycle oil.

A second aspect includes the process of the first aspect in which the hydrogen stream from the methane cracker is provided to the hydrotreater.

A third aspect includes the process of the first or second aspect in the C1 stream from the second separator unit is recycled to the methane cracker for further methane cracking.

A fourth aspect includes the process of any of the first through third aspects in which the hydrogen fraction from the second separator unit is recycled to the methane cracker or to the hydrotreater.

A fifth aspect includes the process of any of the first through fourth aspects in which the C2 stream from the second separator unit is recycled to the ethane steam cracker for further conversion to light olefins.

A sixth aspect includes the process of any of the first through fifth aspects in which the C3-C4 alkane stream from the second separator unit is recycled to the dehydrogenation reactor for further conversion to propylene and butenes.

A seventh aspect includes the process of any of the first through sixth aspects in which the residual stream comprising cracked naphtha, light cycle oil and heavy cycle oil from the second separator unit is recycled to the hydrotreater for further processing.

An eighth aspect includes the process of any of the first through seventh aspects in which the solvent deasphalting unit is operated at a temperature ranging from 120° C. to 160° C. and a pressure ranging from 1 to 40 bar.

A ninth aspect includes the process of any of the first through eighth aspects in which a coke drum in the delayed coker unit is operated at a temperature ranging from 470° C. to 505° C. and a pressure ranging from 1 to 2 bar.

A tenth aspect includes the process of any of the first through ninth aspects in which the hydrotreater is operated at a temperature ranging from 280° C. to 450° C. and a pressure ranging from 5 to 160 bar.

An eleventh aspect includes the process of any of the first through tenth aspects in which the methane cracker is operated at a temperature ranging from 700° C. to 1,000° C.

A twelfth aspect includes the process of any of the first through eleventh aspects in which the ethane steam cracker is operated at a temperature ranging from 800° C. to 950° C.

A thirteenth aspect includes the process of any of the first through twelfth aspects in which the dehydrogenation reactor is operated at a temperature ranging from 575° C. to 620° C. and a pressure ranging from 1 to 5 bar.

A fourteenth aspect includes the process of any of the first through thirteenth aspects in which the aromatization unit is operated at a temperature ranging from 204° C. to 540° C. and a pressure ranging from 0.345 to 10 bar.

A fifteenth aspect includes the process of any of the first through fourteenth aspects in which the steam enhanced catalytic cracking unit is operated at a temperature ranging from 600° C. to 750° C. and a pressure ranging from 1 to 20 bar.

A sixteenth aspect includes the process of any of the first through fifteenth aspects in which the hydrotreater product stream comprises less than 800 ppm nitrogen and less than 900 ppm sulfur.

A seventeenth aspect includes the process of any of the first through sixteenth aspects in which the first separator unit comprises a plurality of separation units.

An eighteenth aspect includes the process of any of the first through seventeenth aspects in which the second separator comprises a plurality of separation units.

A nineteenth aspect includes the process of any of the first through eighteenth aspects in which the deasphalted oil product is provided to the steam enhanced catalytic cracking unit.

A twentieth aspect includes the process of any of the first through nineteenth aspects in which the delayed coker product stream is separated into a first delayed coker product stream and a second delayed coker product stream comprising C5 to hydrocarbons boiling at 343° C., the remainder of the delayed coker product stream in the first delayed coker product stream, with the first delayed coker product stream provided to the hydrotreater and the second delayed coker product stream provided to the steam enhanced catalytic cracking unit.

According to a twenty-first aspect, an integrated system for conversion of crude oil to value added petrochemicals includes (i) a feed separator to separate a hydrocarbon stream comprising the crude oil into a light crude fraction boiling at a first temperature or less and a heavy crude fraction boiling at greater than the first temperature, wherein the first temperature is between 190 and 210° C.; (ii) a solvent deasphalting unit fluidly connected to the feed separator to receive the heavy crude fraction boiling at a temperature greater than the first temperature from the feed separator, wherein residue heavy components having a boiling points above 300° C. and asphaltenes are removed from the heavy crude fraction to generate a pitch product comprising the asphaltenes and residue heavy components and a deasphalted oil product; (iii) a delayed coker unit fluidly connected to the solvent deasphalting unit to receive the pitch product, wherein the pitch product undergoes thermal cracking reaction to obtain solid petroleum coke and a delayed coker product stream comprising C1-C4 light gases, coker naphtha, and coker gas oil; (iv) a hydrotreater fluidly connected to the feed separator, the solvent deasphalting unit, and the delayed coker to receive the light crude fraction boiling at the first temperature or less, the deasphalted oil product, and the delayed coker product stream, wherein the light crude fraction, the deasphalted oil product, and the delayed coker product stream are hydrotreated to remove heteroatoms and saturate carbon-carbon bonds to generate a hydrotreater product stream; (v) a first separator unit fluidly connected to the hydrotreater to receive the hydrotreater product stream, wherein the hydrotreater product stream is separated into a C1 fraction, a C2 fraction, a C3-C4 fraction, a hydrotreated light fraction comprising C5 hydrocarbons to hydrocarbons boiling at less than a second temperature, and a hydrotreated heavy fraction comprising hydrocarbons boiling at the second temperature or greater; (vi) a methane cracker fluidly connected to the first separator unit to receive the C1 fraction, wherein the C1 fraction is converted to a hydrogen stream and a fixed carbon stream; (vii) an ethane steam cracker fluidly connected to the first separator to receive the C2 fraction, wherein the C2 fraction is cracked to generate an ethane steam cracker product stream comprising light olefins and aromatics; (viii) a dehydrogenation reactor fluidly connected to the first separator to receive the C3-C4 fraction, wherein the C3-C4 fraction is dehydrogenated to generate a dehydrogenated product stream comprising propylene and butenes generated from propane and butanes in the C3-C4 fraction; (ix) an aromatization unit fluidly connected to the first separator to receive the hydrotreated light fraction, wherein the aromatization unit converts aliphatic hydrocarbons in the hydrotreated light fraction to aromatics to generate an aromatization product stream; (x) a steam enhanced catalytic cracking unit fluidly connected to the first separator to receive the hydrotreated heavy fraction comprising hydrocarbons boiling at the second temperature or greater, wherein the hydrotreated heavy fraction is cracked to generate a SECC product stream comprising light olefins; and (xi) a second separator fluidly connected to the ethane steam cracker, the dehydrogenation reactor, the aromatization unit, and the steam enhanced catalytic cracking unit to receive the ethane steam cracker product stream, the dehydrogenated product stream, the aromatization product stream, and the SECC product stream, wherein the second separator unit splits the ethane steam cracker product stream, the dehydrogenated product steam, the aromatization product stream, and the SECC product stream into a hydrogen fraction, a C1 stream, a C2 stream, a C3-C4 alkane stream, a light olefin stream, a BTX stream comprising benzene, toluene, and xylene, and a residual stream comprising cracked naphtha, light cycle oil and heavy cycle oil.

A twenty-second aspect includes the system of the twenty-first aspect in which the hydrogen stream from the methane cracker is fluidly connected to the hydrotreater such that the hydrogen stream is provided as a feed stream to the hydrotreater.

A twenty-third aspect includes the system of the twenty-first or twenty-second aspect in which the C1 stream from the second separator unit is fluidly connected to the methane cracker such that the C1 stream is recycled to the methane cracker for further methane cracking.

A twenty-fourth aspect includes the system of any of the twenty-first through twenty-third aspects in which the C2 stream from the second separator unit is fluidly connected to the ethane steam cracker such that the C2 stream is recycled to the ethane steam cracker for further conversion to light olefins.

A twenty-fifth aspect includes the system of any of the twenty-first through twenty-fourth aspects in which the C3-C4 alkane stream from the second separator unit is fluidly connected to the dehydrogenation reactor such that the C3-C4 alkane stream is recycled to the dehydrogenation reactor for further conversion to propylene and butenes A twenty-sixth aspect includes the system of any of the twenty-first through twenty-fifth aspects in which the residual stream comprising cracked naphtha, light cycle oil and heavy cycle oil from the second separator unit is fluidly connected to the hydrotreater such that the residual stream is recycled to the hydrotreater for further processing.

It should be apparent to those skilled in the art that various modifications and variations can be made to the described embodiments without departing from the spirit and scope of the claimed subject matter. Thus, it is intended that the specification cover the modifications and variations of the various described embodiments provided such modifications and variations come within the scope of the appended claims and their equivalents.

For purposes of this disclosure, it is explicitly noted that indication that one stream or effluent is passed or provided from one unit to another unit includes embodiments where the stream or effluent is passed directly from one unit to another unit as well as embodiments where there is an intervening system or unit which may substantially change the composition of the stream or effluent between the units. As used in the present disclosure, passing a stream or effluent from one unit "directly" to another unit refers to passing the stream or effluent from the first unit to the second unit without passing the stream or effluent through an intervening reaction system or separation system that substantially changes the composition of the stream or effluent. Similarly, indication that two systems are "fluidly connected" indicates that streams may be passed directly between the systems. Heat transfer devices, such as heat exchangers, preheaters, coolers, condensers, or other heat transfer equipment, and pressure devices, such as pumps, pressure regulators, compressors, or other pressure devices, are not considered to be intervening systems that change the composition of a stream or effluent. Combining two streams or effluents together also is not considered to comprise an intervening system that changes the composition of one or both of the streams or effluents being combined.

It should further be understood that streams may be named for the components of the stream, and the component for which the stream is named may be the major component of the stream (such as comprising from 50 weight percent (wt. %), from 70 wt. %, from 90 wt. %, from 95 wt. %, from 99 wt. %, from 99.5 wt. %, or even from 99.9 wt. % of the contents of the stream to 100 wt. % of the contents of the stream). It should also be understood that components of a stream are disclosed as passing from one system component to another when a stream comprising that component is disclosed as passing from that system component to another. For example, a disclosed "hydrocarbon stream" passing to a first system component or from a first system component to a second system component should be understood to equivalently disclose "hydrocarbon" passing to the first system component or passing from a first system component to a second system component.

The singular forms "a", "an" and "the" include plural referents, unless the context clearly dictates otherwise.

Throughout this disclosure ranges are provided. It is envisioned that each discrete value encompassed by the ranges are also included. Additionally, the ranges which may be formed by each discrete value encompassed by the explicitly disclosed ranges are equally envisioned. For brevity, the same is not explicitly indicated subsequent to each disclosed range and the present general indication is provided.

As used in this disclosure and in the appended claims, the words "comprise," "has," and "include" and all grammatical variations thereof are each intended to have an open, non-limiting meaning that does not exclude additional elements or steps.

What is claimed is:

1. An integrated process for conversion of crude oil to value added petrochemicals, the process comprising:
   (i) providing a hydrocarbon stream comprising the crude oil to a feed separator to separate the hydrocarbon stream into a light crude fraction boiling at a first temperature and a heavy crude fraction boiling at greater than the first temperature, wherein the first temperature is between 190 and 210° C.;
   (ii) providing the heavy crude fraction to a solvent deasphalting unit to generate a pitch product comprising asphaltenes and residue heavy components having boiling points above 300° C. and a deasphalted oil product;
   (iii) providing the pitch product to a delayed coker unit, wherein the pitch product undergoes a thermal cracking reaction to obtain a solid petroleum coke stream and a delayed coker product stream comprising C1-C4 light gases, coker naphtha, and coker gas oil;
   (iv) providing the light crude fraction, the deasphalted oil product, and the delayed coker product stream to a hydrotreater to remove heteroatoms and saturate carbon-carbon bonds to generate a hydrotreater product stream;
   (v) providing the hydrotreater product stream to a first separator, wherein the hydrotreater product stream is separated into a C1 fraction, a C2 fraction, a C3-C4 fraction, a hydrotreated light fraction comprising C5 hydrocarbons to hydrocarbons boiling at a second temperature, and a hydrotreated heavy fraction comprising hydrocarbons boiling at or greater than the second temperature, wherein the second temperature is between 200 and 215° C.;
   (vi) providing the C1 fraction to a methane cracker, wherein the C1 fraction is converted to a hydrogen stream and a fixed carbon stream;
   (vii) providing the C2 fraction to an ethane steam cracker, wherein the C2 fraction is cracked to generate an ethane steam cracker product stream comprising light olefins and aromatics;
   (viii) providing the C3-C4 fraction to a dehydrogenation reactor, wherein the C3-C4 fraction is dehydrogenated to generate a dehydrogenated product stream comprising propylene and butenes generated from propane and butanes in the C3-C4 fraction;
   (ix) providing the hydrotreated light fraction to an aromatization unit, wherein the aromatization unit converts aliphatic hydrocarbons in the hydrotreated light fraction to aromatics to generate an aromatization product stream;
   (x) providing the hydrotreated heavy fraction to a steam enhanced catalytic cracking unit (SECC), wherein the hydrotreated heavy fraction is cracked to generate a SECC product stream comprising light olefins; and
   (xi) providing the ethane steam cracker product stream, the dehydrogenated product stream, the aromatization product stream, and the SECC product stream to a second separator to obtain a hydrogen fraction, a C1 stream, a C2 stream, a C3-C4 alkane stream, a light olefin stream, a BTX stream comprising benzene, toluene, and xylene, and a residual stream comprising cracked naphtha, light cycle oil and heavy cycle oil.

2. The process of claim 1, wherein the hydrogen stream from the methane cracker is provided to the hydrotreater.

3. The process of claim 1, wherein the C1 stream from the second separator is recycled to the methane cracker for further methane cracking.

4. The process of claim 1, wherein the hydrogen fraction from the second separator is recycled to the methane cracker or to the hydrotreater.

5. The process of claim 1, wherein the C2 stream from the second separator is recycled to the ethane steam cracker for further conversion to light olefins.

6. The process of claim 1, wherein the C3-C4 alkane stream from the second a separator is recycled to the dehydrogenation reactor for further conversion to propylene and butenes.

7. The process of claim 1, wherein the residual stream from the second separator is recycled to the hydrotreater for further processing.

8. The process of claim 1, wherein a portion of the deasphalted oil product is provided directly to the steam enhanced catalytic cracking unit.

9. The process of claim 1, wherein the delayed coker product stream is separated into a first delayed coker product stream and a second delayed coker product stream comprising C5 hydrocarbons to hydrocarbons boiling at a temperature of 343° C. wherein the first delayed coker product stream is provided to the hydrotreater and the second delayed coker product stream is provided to the steam enhanced catalytic cracking unit.

10. The process of claim 1, wherein the solvent deasphalting unit is operated at a temperature ranging from 120° C. to 160° C. and a pressure ranging from 1 to 40 bar.

11. The process of claim 1, wherein a coke drum in the delayed coker unit is operated at a temperature ranging from 470° C. to 505° C. and a pressure ranging from 1 to 2 bar.

12. The process of claim 1, wherein the hydrotreater is operated at a temperature ranging from 280° C. to 450° C. and a pressure ranging from 5 to 160 bar.

13. The process of claim 1, wherein the aromatization unit is operated at a temperature ranging from 400° C. to 600° C. and a pressure ranging from 1 to 35 bar.

14. The process of claim 1, wherein the steam enhanced catalytic cracking unit is operated at a temperature ranging from 600° C. to 750° C. and a pressure ranging from 1 to 20 bar.

15. The process of claim 1, wherein the hydrotreater product stream comprises less than 800 ppm nitrogen and less than 900 ppm sulfur.

16. The process of claim 1, wherein the first separator comprises a plurality of separation units.

17. The process of claim 1, wherein the second separator comprises a plurality of separation units.

\* \* \* \* \*